United States Patent
Zanellato et al.

(10) Patent No.: US 10,821,131 B2
(45) Date of Patent: Nov. 3, 2020

(54) PHARMACEUTICAL FORMULATIONS COMPRISING CHONDROITIN SULFATE AND HYALURONIC ACID DERIVATIVES

(71) Applicant: FIDIA FARMACEUTICI S.p.A., Abano Terme (PD) (IT)

(72) Inventors: Anna Maria Zanellato, Abano Terme (IT); Vincenza Corsa, Abano Terme (IT); Giancarlo Carpanese, Abano Terme (IT); Monica Campisi, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 15/489,299

(22) Filed: Apr. 17, 2017

(65) Prior Publication Data

US 2017/0216344 A1    Aug. 3, 2017

Related U.S. Application Data

(62) Division of application No. 14/389,301, filed as application No. PCT/IB2013/052443 on Mar. 27, 2013, now Pat. No. 9,655,918.

(30) Foreign Application Priority Data

Mar. 30, 2012   (IT) ............... PD2012A0098

(51) Int. Cl.
| | |
|---|---|
| *A61K 31/726* | (2006.01) |
| *A61K 31/728* | (2006.01) |
| *A61P 19/02* | (2006.01) |
| *A61K 31/737* | (2006.01) |
| *C08B 37/08* | (2006.01) |
| *C08B 37/00* | (2006.01) |
| *A61K 9/00* | (2006.01) |
| *A61K 9/08* | (2006.01) |
| *A61P 13/10* | (2006.01) |
| *A61K 47/02* | (2006.01) |

(52) U.S. Cl.
CPC .......... *A61K 31/737* (2013.01); *A61K 9/0019* (2013.01); *A61K 9/08* (2013.01); *A61K 31/726* (2013.01); *A61K 31/728* (2013.01); *A61K 47/02* (2013.01); *A61P 13/10* (2018.01); *A61P 19/02* (2018.01); *C08B 37/0069* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 5,972,909 A | * | 10/1999 | Di Napoli ............ A61K 31/728 514/54 |
| 6,979,679 B2 | | 12/2005 | Marcum |
| 7,504,387 B2 | | 3/2009 | Marcum |
| 7,863,256 B2 | | 1/2011 | Schiavinato et al. |
| 9,655,918 B2 | * | 5/2017 | Zanellato ............ A61K 31/737 |
| 2004/0214793 A1 | | 10/2004 | Hermida Ochoa |
| 2012/0237610 A1 | | 9/2012 | Thorel et al. |

FOREIGN PATENT DOCUMENTS

| | | |
|---|---|---|
| EP | 1 095 064 B1 | 6/2005 |
| WO | WO 03/053453 A1 | 7/2003 |
| WO | WO 2007/138014 A1 | 12/2007 |

OTHER PUBLICATIONS

Mathieu et al., "Rheologic Behavior of Osteoarthritic Synovial Fluid after Addition of Hyaluronic Acid" Clin Orthop Relat Res vol. 467 pp. 3002-3009 (Year: 2009).*
Finelli et al., :A new viscosupplement based on partially hydrophobic hyaluronic acid: A comparative study Biorheology vol. 48 pp. 263-275 (Year: 2011).*
Mensitieri et al., "Viscoelastic evaluation of different knee osteoarthritis therapies" Journal of Materials Science: Materials in Medicine vol. 6 pp. 130-137 (Year: 1995).*
Borzacchiello et al., "Effect of hyaluronic acid amide derivative on equine synovial fluid viscoelasticity" Journal of Biomedical Materials Research Published Mar. 25, 2009, pp. 1162-1170 (Year: 2009).*
Borzacchiello et al., "Effect of hyaluronic acid amide derivative on equine synovial fluid viscoelasticity", Part A Mar. 1, 2010, vol. 92, No. 3, Mar. 1, 2010 (Mar. 1, 2010), pp. 1162-1170, XP-002711289.
International Search Report, issued in PCT/IB2013/052443, dated Aug. 28, 2013.
Written Opinion of the International Searching Authority, issued in PCT/IB2013/052443, dated Aug. 28, 2013.
Finelli et al., "Gel-Like Structure of a Hexadecyl Derivative of Hyaluronic Acid for the Treatment of Osteoarthritis", Macromolecular Bioscience Jul. 7, 2009, vol. 9, No. 7, Jul. 7, 2009 (Jul. 7, 2009), pp. 646-653, XP-002711290.
International Preliminary Report on Patentability issued in International Application No. PCT/IB2013/052443 dated Oct. 9, 2014.

* cited by examiner

*Primary Examiner* — Eric Olson
(74) *Attorney, Agent, or Firm* — Birch, Stewart, Kolasch & Birch, LLP

(57) ABSTRACT

The present invention relates to pharmaceutical formulations containing a combination of specific high-molecular weight hyaluronic acid derivatives and chondroitin sulfate to be used in the treatment of osteoarthritis, of subchondral damage, osteoporosis, synovitis, tenosynovitis, tendinitis, tendinosis, as an intra-articular washing liquid and as a viscous substitute of synovial fluid following osteochondral surgery. These formulations are also suitable for the treatment of interstitial cystitis.

4 Claims, 4 Drawing Sheets

PHARMACEUTICAL FORMULATIONS COMPRISING CHONDROITIN SULFATE AND HYALURONIC ACID DERIVATIVES

CROSS REFERENCE TO RELATED APPLICATIONS

This application is a Division of copending application Ser. No. 14/389,301, filed on Sep. 29, 2014, which is a 371 National Stage of PCT International Application No. PCT/IB2013/052443 which was filed on Mar. 27, 2013, which claims priority to Italian Application No. PD2012A000098 which was filed on Mar. 30, 2012, all of which are hereby expressly incorporated by reference into the present application.

FIELD OF THE INVENTION

The present invention relates to pharmaceutical formulations for use in the treatment of osteoarthritis, subchondral damage, osteoporosis, synovitis, tenosynovitis, tendinitis, tendinosis, interstitial cystitis and finally also as an intra-articular washing liquid and/or as a viscous substitute for synovial fluid following osteochondral surgery.

STATE OF THE ART

The cartilage matrix is composed of a three-dimensional structure made of collagen molecules and complex proteoglycan aggregates which are, in turn, composed of a hyaluronic acid (HA)-based support structure interacting with molecules of glycosaminoglycans (GAG) non-convalently bound to polypeptide sequences, thus conferring to cartilage both biomechanical and viscoelastic properties.

In fact, HA is a molecule exhibiting specific viscoelastic properties, primarily synthesized and secreted in the joint cavity by synoviocytes (Asari A. et al., Arch Histol Cytol, 1995, 58(1):65-76) and, for the aforementioned reasons, it is one of the main components of synovial liquid exhibiting both viscous and elastic properties depending on the number and the molecular weight (MW) of the HA molecules contained therein.

The viscoelastic nature of the synovial liquid is, therefore, related to the HA content present in the joint cavity and its concentration varies with age: in fact, in human beings it already begins to decrease after the age of 25. The viscoelastic features of synovial liquid may be quantified by the measurement of its moduli: the first modulus is called G' or elastic modulus because it represents the energy stored when the polysaccharide is subjected to strain/deformation, the second modulus is defined G" or viscous modulus since it represents the energy which is dissipated when the molecule is subjected to strain: briefly, G' imparts elasticity to the synovial fluid, while G" is an index of the resistance to friction between two joint surfaces, therefore of resistance to a strain which may determine the deformation of articular cartilage.

During slow movements, HA acts as a viscous lubricant (a property which is imparted by its G" modulus), while during fast movements it absorbs with elastic properties any traumas or microtraumas which may affect the joint.

Osteoarthrosis/osteoarthritis (OA) is a highly disabling disease characterized by a progressive erosion of articular cartilages due to the degradation of the articular matrix and to the loss of cellular components.

It is well known how the mechanical unbalance that can involve the joint in its entirety may be the initial cause of the onset of the above-mentioned disease.

This joint instability may substantially be caused by different factors (such as trauma, inflammation of the joint system, cartilage erosion, incorrect deambulation or posture) and may determine an alteration of the delicate balance existing between synthesis and degradation of the extracellular matrix primarily synthesized by chondrocytes and synoviocytes.

When this situation of perfect but delicate homeostasis is compromised, the degradation of the matrix outperforms its synthesis and, as a result, it starts a slow but progressive process of degradation, which is poorly compensated by the corresponding process of synthesis following the loss of chondrocytes.

In fact, an excessive and/or incorrect load onto the joints may cause a chondrocyte response, which is expressed in the synthesis of those enzymes responsible for the degradation of the cartilage itself (called Metalloproteases (MMPs)) synthesized by chondrocytes when stimulated by inflammatory cytokines such as IL-1 and TNF-α, which are produced and released in the joint cavity especially upon the onset of an inflammatory disease such as OA. In fact, IL-1 stimulates the synthesis of high levels of nitric oxide and inhibits the synthesis of proteoglycans by the chondrocytes themselves (Dozin B. et al., Matrix Biology, 2002, 21:449-459). Inflamed cartilage further produces high quantities of COX-2 which, in turn, determines the overproduction and release in the joint cavity of $PGE_2$ which contributes to exacerbating the degree of inflammation, and, thus, cartilage damage (Amin A. et al., J Clin Invest, 1997, 99:1231).

In acute and chronic inflammation and in the major degenerative processes of joints (OA), the concentration and molecular weight (MW) of the HA present in the joint synovial fluid significantly decreases thus compromising its lubricant ability. It is well known that the functional features of synovial liquid depend on both the concentration and the degree of polymerization of HA, and that their alterations may determine a joint histological damage of the OA-type.

In fact, the synovial fluid of OA joints cannot efficiently protect synovial tissue and articular cartilage from the "negative" effects of the mechanical stresses which are exerted on joints on a daily basis: in non-pathological synovial fluids upon increase of the strain frequency, the two moduli normally increase: at a low frequency the viscous component prevails, while at a high frequency the value of the elastic modulus is greater than the viscous one; on the other hand, in the synovial liquid of OA joints G' and G" values significantly lower than normal are found.

The HA exchange within non-pathological synovial liquid is generally very fast, while in OA both its drop in concentration (associated to a decrease in GAG), both a decrease in its MW as well as a sharp reduction in its exchange flow have been found (Balazs E A. et al, J Rheumatol Suppl, 1993, 12:75-82; Belcher C. et al, Annals of the Rheumathic Disease, 1997, 56:299-307).

For these reasons, Balazs was the first to suggest the possibility of modifying the evolution of the osteoarthrosic process via the intake of exogenous HA directly within the joint cavity.

Various drugs are currently commercially available for the intra-articular administration of HA in OA, among which are: Hyalgan®, HA purified from cockscomb with MW:5-7.3×10$^5$ Da (U.S. Pat. No. 5,925,626), Synvisc®, (Hylan G-F 20) HA cross-linked with formaldehyde and divinyl sulfone with MW:6-7×10⁶ Da (U.S. Pat. No. 4,713,448), Artz®, HA with MW:6.2-1.2×10⁵ Da.

Consolidated clinical data have shown how intra-articularly injected HA carries out a significant viscosupplementation action, that improves the functional abilities of the limb affected by the OA disease, with a consequent reduction in articular pain.

HA is a heteropolysaccharide composed of alternating residues of D-glucuronic acid and N-acetyl-D-glucosamine. It is a linear chain polymer with a MW that may range between 50,000 and 13×10⁶ Da, depending on the source it is obtained from and the methods of preparation used. It is found in nature in pericellular gels, in the fundamental substance of the connective tissue of vertebrate organisms (of which it is one of the main components), in the synovial fluid of joints, in vitreous humor and in the umbilical cord. It is well known how HA, by means of its membrane receptor CD44, modulates many and various processes related to cell physiology and biology such as, for instance, cell proliferation, migration, differentiation and angiogenesis, and how it also carries out other functions such as tissue hydration and joint lubrication.

Recently, the intra-articular use of chondroitin sulfate (CS) as an anti-inflammatory agent of the OA joint has been successfully experimented: a constituent of matrix proteoglycans, in non-pathological situations it contributes to hydrating cartilages and imparts resistance against mechanical compression; its ability to reduce the expression of MMPs in chondrocytes of OA joints, and its ability to induce high-MW HA synthesis in OA synovial fibroblasts have also been shown (David-Raoudi M et al., Glycobiology, 2009, 19:813-815).

It is a sulfated glycosaminoglycan composed of disaccharide units made of N-acetyl-galactosamine and D-glucuronic acid wherein the majority of galactosamine residues are sulfated at position 4 or 6, by making the polysaccharide highly anionic. CS has also proved capable of reducing osteoclast activity, thus reducing bone reabsorption in general and, in a particular way, subchondral reabsorption, a process involving both the initial and final stages of OA; osteoclast activation is crucial also in "transient regional osteoporosis", a potentially disabling disease determining focal osteopenia and inflammation (Massara A. et al., Reumatismo, 2005, 57:5-15). Furthermore, CS has been tested with good results also in inflammatory diseases such as synovitis and tendinitis (Wildi L M. et al., Ann Rheum Dis, 2011, 70:982-989).

For the afore-mentioned anti-inflammatory properties, CS has been initially investigated in ophthalmic surgery in combination with HA of a specific MW, combined in aqueous buffers at specific weight ratios (U.S. Pat. No. 6,051,560). CS in combination with HA of a MW in the range of 500-750 KD has been investigated with remarkable success also as an intra-articular stage I and II therapy of OA, in a weight ratio of 4:3 with HA, in phosphate and sodium chloride buffer, with an overall final viscosity comprised between 68 and 115 cps measured at 1 sec-1 at 25° C., for an overall therapy of 2-6 injections for a period of therapeutic efficacy of 1-3 months (EP1443945).

Finally, viscosity changes of viscoelastic fluids composed of a combination of CS and HA are well known to those skilled in the art: the experimental results show how CS increases the viscosity of low-MW HA solutions (vs. formulations containing only HA at the same concentration), although the viscosity of CS is very low and irrelevant vs. that of HA; however, the two moduli G' and G" of HA solutions are not modified following the addition of CS (Nishimura M. et al., Biochimica et Biophysica Acta, 1998, 1380:1-9).

Interstitial cystitis is a bladder disease which shows with pain or soreness, frequent urination, suprapubic pain and chronic pelvic pain.

In spite of its name, interstitial cystitis is quite different from common cystitis (caused by specific bacteria), symptoms are similar, however, no bacterial infections arise and, in fact, antibiotic therapy proves ineffective.

The etiology of interstitial cystitis is not known, it is believed to be caused by the absence of glycosaminoglycans in the mucous layer coating the bladder. Cellular alteration of bladder walls is therefore found with lesions to the inner epithelium which, in contact with the acids present in urines, cause an increase in the local nerve sensitivity regulating pain and increases the reception of the stimulus to urinate.

Based on this hypothesis as a clinical therapy there have been introduced Pentosan Polysulfate, Heparin and Hyaluronic Acid (Cystistat) which is instilled within the bladder to reconstruct and protect the inner epithelium.

SUMMARY OF THE INVENTION

The Applicant has now found that it is possible to overcome the above-mentioned drawbacks of the formulations known in the art according to the present invention thanks to formulations containing a combination of high-molecular weight hyaluronic acid derivatives and chondroitin sulfate as best described in the claims appended to the present invention and also described in greater detail below in the detailed description of the invention.

DETAILED DESCRIPTION OF THE INVENTION

Figure 1:
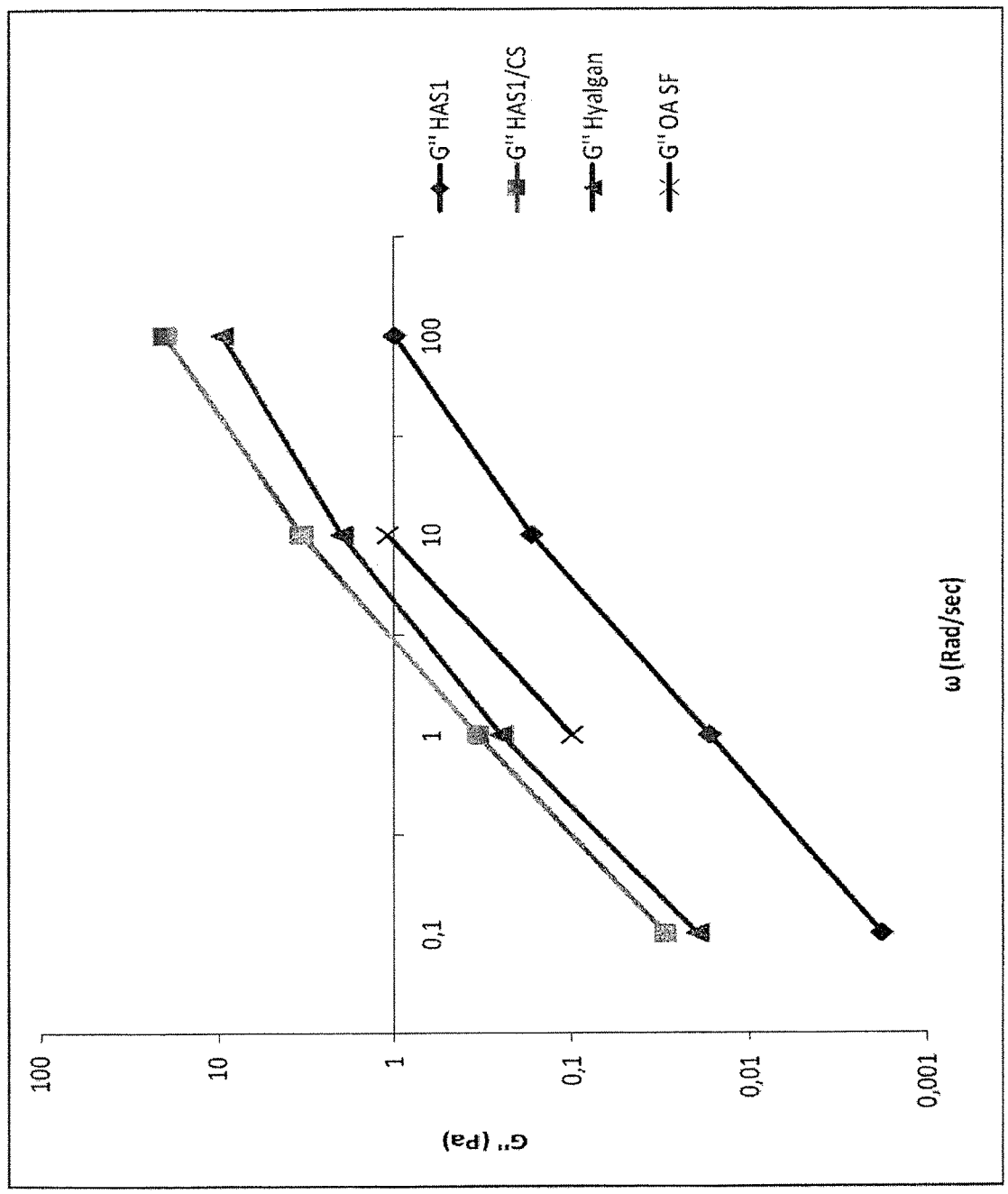
FIG. 1 shows G" values in Pa in function of a) in Rad/sec tested on substances as reported in Example 1.

Object of the present invention are pharmaceutical formulations comprising CS in combination with HA derivatives selected from:
- HA salified with alkaline or earth alkaline metals, of a weight average MW comprised between 1500-3000 KD, preferably between 2500-3000 KD (HA-HMW; measured before the sterilization process which may be carried out according the techniques known in the art);
- HYADD®: HA amides with amines of the aliphatic, araliphatic, cycloaliphatic, aromatic, cyclic and heterocyclic series, with a (molar) degree of amidation in the range from 0.1 to 10% (HPLC), the HA amide with hexadecylamine with a percentage of amidation comprised between 1 and 8% is preferred (EP 1095064);
- HA O-sulfated derivatives of the 1st degree of sulfation: HAS1, (WO95/25751A1) where first degree of sulfation means the average number of sulfated hydroxyls per hyaluronic acid polymeric unit, i.e. the disaccharide repeating unit (D-glucuronic acid and N-acetylglucosamine)

ACP®: HA inner esters (defined as autocross-linked HA) with a percentage of esterification not greater than 10%, preferably between 1 and 5% esterification (EP 341745);

HA derivatives consisting of the mixture of (i) ACP® and (ii) HBC. wherein (ii) is HA cross-linked with 1,4-butanedioldiglycylether (BDDE), wherein the weight ratio (i)/(ii) is comprised between 10:90 and 90:10, preferably in a weight ratio (i): (ii) of 25:75; (WO2011/023355).

These novel pharmaceutical compositions exhibit rheological features which are completely different from the starting HA derivatives and from the compositions consisting of HA and CS previously described and therefore known in the art. In fact, these novel compositions show important rheological modifications in the G' and G" moduli with respect to the starting derivative, with the same concentration and analytic condition.

This result is entirely unexpected, since, on the other hand, the data (cited above) known to those skilled in the art have shown, in a clear and unequivocal way, that the HA elastic and viscous moduli are not modified at all by the addition of CS (Nishimura M. et al, Biochimica et Biophysica Acta, 1998, 1380:1-9).

The results obtained by the Applicant have instead shown how:
the combination of CS and HAS of the 1st degree of sulfation determines a highly significant increase in the viscous modulus G" of the novel pharmaceutical composition HAS1/CS, imparting rheological features thereto which are specific to a viscosupplementation agent (greater than Hyalgan®, shown below), while associating synergistically with each another both the known anti-inflammatory properties of CS and the anti-inflammatory abilities of HAS 1.

For all the other HA derivatives claimed above, their combination with CS (HYADD®/CS, ACP+HBC/CS, ACP/CS and HA-HMW/CS compositions) has determined a significant decrease in the value of the elastic modulus G', leaving the viscous modulus G" unchanged: consequently, the novel pharmaceutical compositions will show rheological features specific to a viscosupplementation agent wherein the viscous component is proportionally increased with respect to the starting derivative, such a novel composition will thus have a greater resistance to friction and will show greater lubricant capabilities, while associating both the known anti-inflammatory properties of CS and the anti-inflammatory abilities specific for HA derivatives to them. For these reasons, the novel combinations of HA derivatives/CS can be used as a viscous or locoregional lubricant for the treatment and/or therapy of diseases by means of intra-articular administration such as:

OA, both in its initial and its chronic stage, therefore both in a stage of active inflammation and in that of chronic inflammation, determining:
the decrease in the degree of joint inflammation and, thus, of cartilage damage thanks to the synergy between the anti-inflammatory properties of the HA derivative and CS,
the recovery of the correct function of synovial fluid for the improvement of the ability to absorb mechanical stresses of the novel pharmaceutical composition which, in this case, acts as a viscosupplementation agent,
greater viscous lubrication of joint surfaces but, most especially, greater ability of the joint itself to resist to friction between joint surfaces; the novel compositions are therefore capable of slowing down/curing the osteoarthrosic process;
subchondral damage, that is, the bone reabsorption determined by osteoclast activation;
osteoporosis, in particular "transient regional osteoporosis";
osteochondral damage from trauma/microtrauma;
synovitis and tenosynovitis, tendinitis and/or tendinosis;
interstitial cystitis: in this case the treatment consists in the intrabladder instillation of the selected composition since, for the novel viscous features described above, the novel formulations show an adhesive ability to the bladder wall which is greater than reference products, and thus ensure protection of the epithelium for long periods of time thus making better clinical results possible.

The Applicant describes and claims the use of such lubricant as a particularly viscous intra-articular washing liquid and as a viscous substitute of synovial fluid following osteochondral surgery (such as, for example, in arthroscopy or in ligament reconstruction).

The Applicant therefore describes and claims novel viscous lubricants comprising CS in combination with the above-mentioned HA derivatives, for use in the intra-articular or locoregional treatment of OA, subchondral damage, transient regional osteoporosis, osteochondral damage, in the treatment of synovitis and tenosynovitis, tendinitis and/or tendinosis.

The Applicant further claims a novel viscous intra-articular washing liquid and a novel viscous substitute of synovial fluid comprising CS in combination with the above-mentioned HA derivatives, for use in the post-surgical treatment of osteochondral surgery.

The therapeutic treatment does not comprise anymore one overall therapy of 2-6 injection for a period of 1-3 months as known in the art but, for the synergistic rheological/anti-inflammatory effects obtained, it is possible to reduce the posology to 1-2 injections for a period of therapeutic effectiveness comprised between 3 and 6 months. The Applicant finally describes and claims novel viscous pharmaceutical compositions comprising CS in combination with the above-mentioned HA derivatives (the composition of HA-HMW/CS and HYADD®/CS is preferred) for use in the intrabladder treatment of interstitial cystitis.

The HA used for the preparation of the claimed derivatives may derive from any source, for example, by extraction from cockscombs (EP138572), by fermentation (for example from Streptocuccus, EP0716688), or by biosynthesis (from Bacillus) as it is known by those skilled in the art, and have a weight average MW comprised between 400 and 3000 KDa, in particular between 1500-3000 KD and preferably between 2500-3000 KD for HA salified with alkaline or alkaline earth metals (HA-HMW), in particular between 500 and 750 KDa for the preparation of the HYADD® derivative, and even more specifically for the HA hexadecylamide with an average degree of amidation comprised between 1 and 8%, between 200 and 750 KDa for the preparation of the HBC derivative, between 150 and 300 KD for the ACP® and HAS1 derivative.

The chondroitin sulfate used for the present invention has a weight average MW comprised between 10-80 KD, is currently produced by extraction of animal and fish (shark and whale) cartilages (for example, the CS used for the experiments described below has been produced by Seikagaku Kogyo, Tokyo), and contains both chondroitin 4-sulfate and 6-sulfate in ratios which may vary according to the starting extraction cartilage.

CS is added and mixed to the HA derivative in weight ratios of HA derivatives:CS comprised between 1:0,1 and 1:6, depending on the derivative selected for the preparation of the novel pharmaceutical composition, the following ratios are particularly preferred:

HAS1 derivative: CS: 1:2-1:6 is preferred, 1:4 is even more preferred;
HYADD® derivative: CS: 1:0, 2-1:1 is preferred;
ACP®+HBC derivative: CS: 1:0, 2-1:1.5 is preferred;
ACP® derivative: CS: 1:0, 2-1:2 is preferred;
HA-HMW derivative: CS: 1:0.5-1:2 is preferred, 1:1 is even more preferred.

The novel pharmaceutical composition is obtained by combining CS in powder form or previously prepared as a solution, with the selected HA derivative, the latter also present in powder form or previously dissolved and, thus, in gel and/or solution form. Generally, the concentration of said active ingredients or the HA derivative and CS in the final formulation is, for example, for the HA derivative typically comprised between 10 mg/ml and 30 mg/ml, preferably between 15 mg/ml and 20 mg/ml, while for CS it is comprised between 10 mg/ml and 40 mg/ml, preferably between 20 mg/ml and 30 mg/ml, for a total content in ml of the HA derivative comprised between 1 and 3 ml, combined with CS also having a total content comprised between 1 and 3 ml.

The two components have to be mixed for the time required for their combination to be completed and homogeneous, therefore they must be subjected to mechanical stirring at a temperature comprised between 25 and 80° C., according to the ratios selected and derivatives prepared, for a time ranging from 1 to 24 hrs; generally a maximum stirring time of 8-10 hrs is sufficient.

Alternatively, the Applicant describes and claims the possible combination of the two components (HA derivatives and CS) at the time of use, that is, just before the intra-articular or locoregional or intrabladder treatment, or, as a further alternative, the separate administration of the two components which combine directly within the treatment site. This type of administration may take place thanks to the aid of particular medical/surgical devices, that make possible the simultaneous but separate compartmenting of the two components within the same device. For these cases, the HA derivatives and CS are prepared separately because the two components combine directly within the treatment site.

The buffers used for all the above-mentioned preparations are preferably selected from:

dibasic sodium phosphate and monobasic sodium phosphate dissolved in water with sodium chloride, or plain sodium chloride, preferably at physiological concentrations, for a pH of the pharmaceutical composition comprised between 6.5 and 7.4, for an osmolarity that has to be comprised between 100 and 350 mOs/l.

The novel preparations of HA derivatives/CS are then sterilized according to the techniques known to those skilled in the art.

By way of mere description and without limitation, some examples of preparation of the novel pharmaceutical compositions of the present invention are reported:

Example 1: Composition HAS1/CS: 1:4

For this experiment, it was used HAS1 prepared as per EP 702699 by using a starting HA (in particular its salt with tetrabutylammonium) with a weight average MW comprised between 150-300 KD.

20 g HAS1 was solubilized in 1 L aqueous buffer formed by monobasic sodium phosphate (0.05 g), dibasic sodium phosphate (0.6 g), sodium chloride (8.5 g) with a pH of 7.4. 80 g CS (Seikagaku Kogyo, Tokyo) having a MW of 50-60 KD was added thereto, the mixture was subjected to mechanical stirring at 40° C. for 1 hr until the complete and homogeneous solubilization of the two components.

The mixture was cooled to room temperature and then its moduli were determined by using a Thermo Haake Mars II Rheometer at 20° C.

The values were measured in Pa from 0.01 to 100 rad/sec, at fixed strain values of 10%. All the samples were processed with the Haake Rheowin Job Manager 4.0 software. Results: FIG. 1 shows how the viscous modulus G" of HAS I/CS has, at all the essayed frequencies, values being extremely higher than the G" values of the starting HAS1 derivative. The viscous modulus of the novel composition is greater than both G" of the synovial fluid of OA patients (from Balazs E., in Disorders of the knee, 1974, 63-75) and G" of the control viscosupplementation agent Hyalgan® at all the essayed frequencies, thus showing a surprising and totally unexpected rheological pattern (specific to the synovial fluid), not initially exhibited by HAS1 (not combined with CS).

Example 2: Composition HYADD®/CS: 1:1

For this experiment, it was used HA hexadecylamide (HYADD) with an average degree of amidation of 5%, prepared as per EP 1095064 by using a starting HA with a weight average MW comprised between 500 and 750 KD.

8 g HYADD was solubilized in 1 L aqueous buffer made from monobasic sodium phosphate (0.11 g), bibasic sodium phosphate (0.45 g), sodium chloride (8.5 g) with a pH of 7.0. 8 g CS (Seikagaku Kogyo, Tokyo) having a MW of 50-60 KD was added thereto, the mixture was subjected to mechanical stirring at 60° C. for 10-12 hrs until the complete and homogeneous solubilization of the two components.

The mixture was cooled to room temperature and then its moduli were determined by using a Thermo Haake Mars II Rheometer at 20° C.

The values were measured in Pa from 0.01 to 100 rad/sec, at fixed strain values of 10%.

Figure 2:
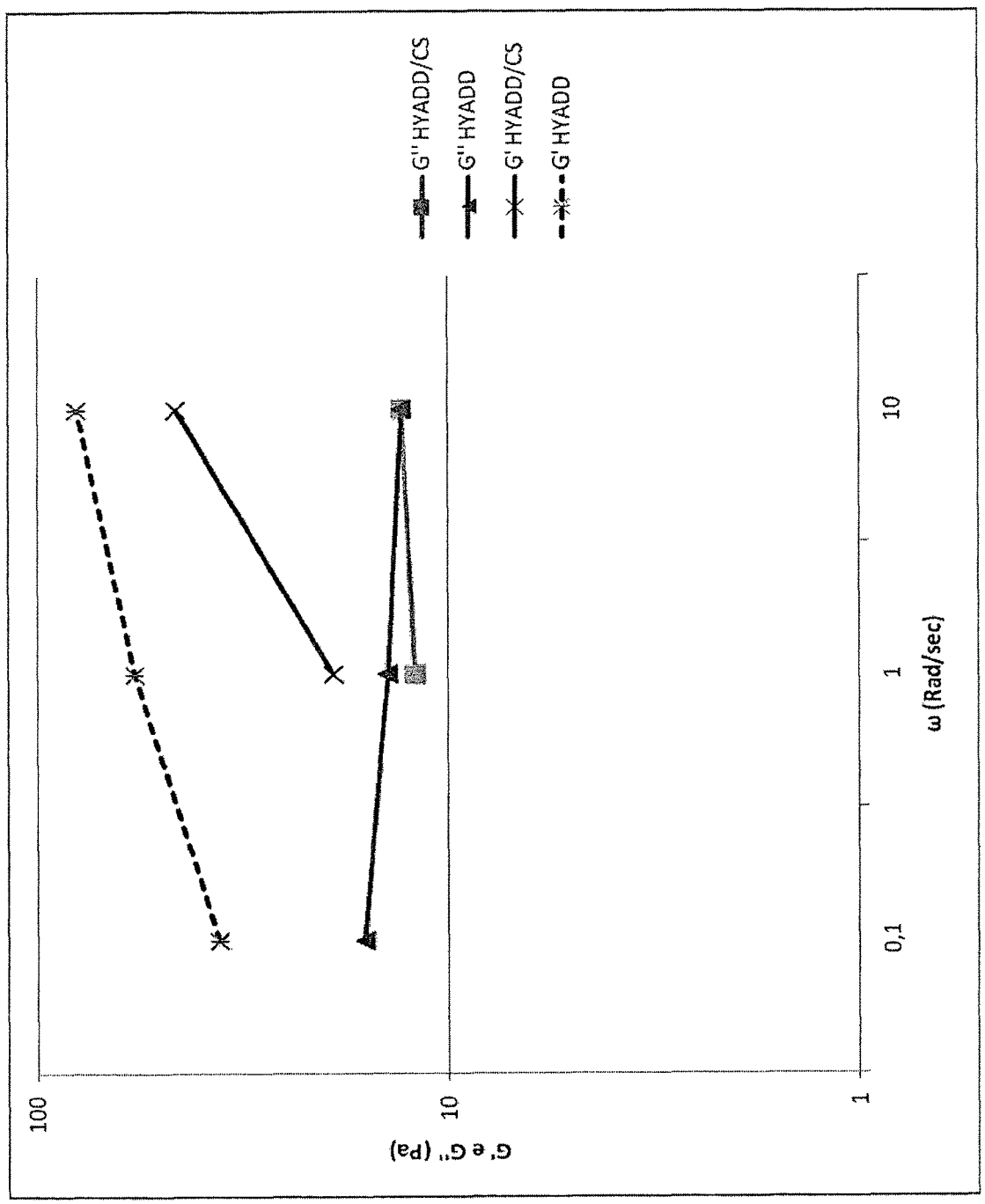
FIG. 2 shows G' and G" values in Pa in function of co in Rad/sec tested on substances as reported in Example 2.

All the samples were processed with the Haake Rheowin Job Manager 4.0 software. Results: FIG. 2 shows how the elastic modulus G' of the novel composition significantly decreases while its viscous modulus G" remains substantially unchanged.

Example 3: Composition ACP®+HBC/CS: 1:1

For this experiment, it was used the ACP+HBC derivative prepared as per Example 12 in WO2011/023355, to obtain 1 L gel containing 25 g ACP+HBC. 25 g CS (Seikagaku Kogyo, Tokyo) having a MW of 50-60 KD was added, the mixture was subjected to mechanical stirring at 40° C. for 1 hr until the complete and homogeneous solubilization of the two components.

The mixture was cooled to room temperature and then its moduli were determined by using a Thermo Haake Mars II Rheometer at 20° C.

The values were measured in Pa from 0.01 to 100 rad/sec, at fixed strain values of 10%.

All the samples were processed with the Haake Rheowin Job Manager 4.0 software.

Figure 3:
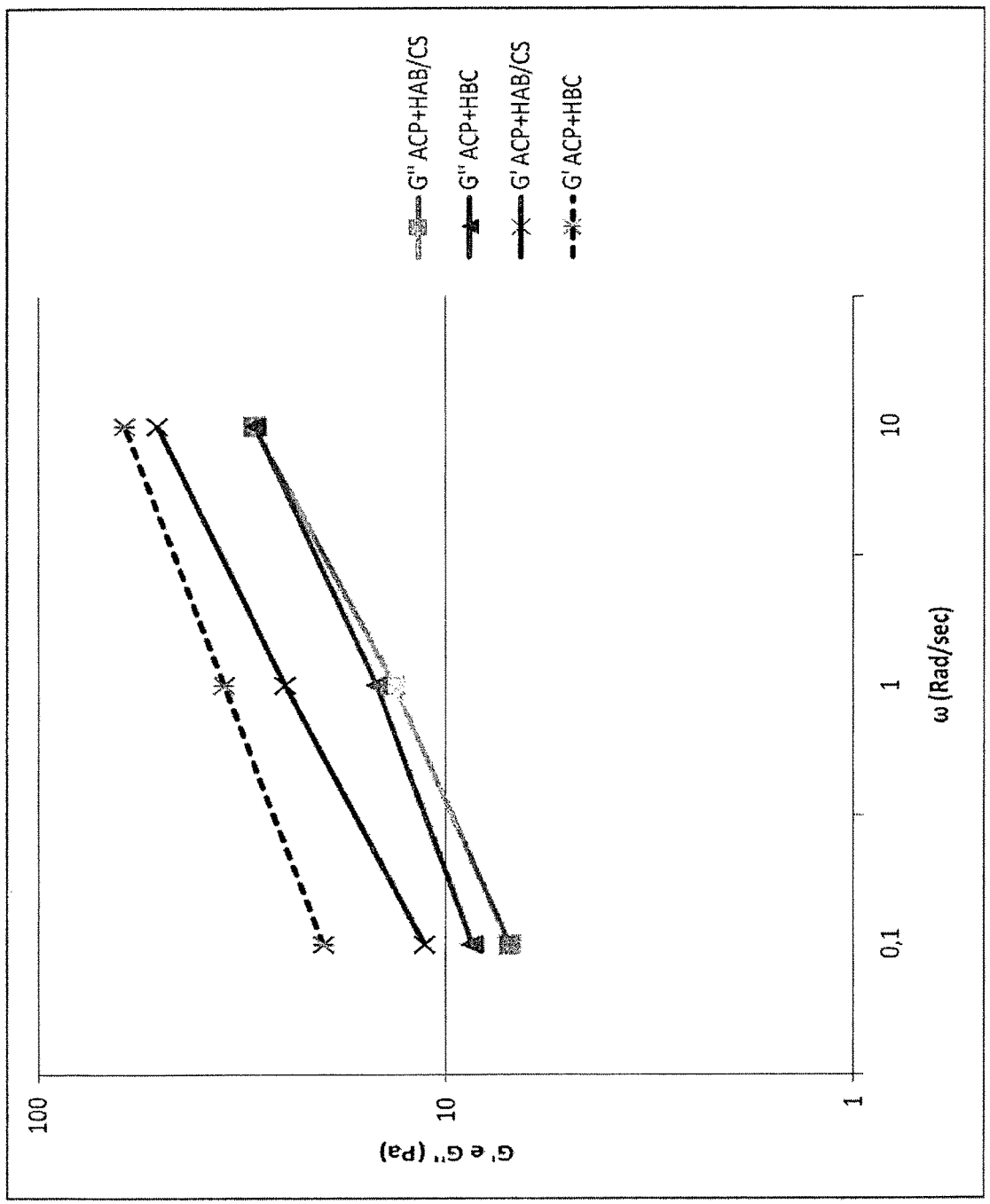
FIG. 3 shows G' and G" values in Pa in function of a) in Rad/sec tested on substances as reported in Example 3.

Results: FIG. 3 shows how also the elastic modulus G' of this novel composition significantly decreases while its viscous modulus G" remains substantially unchanged.

Example 4: Composition HA-HMW/CS: 1:1

For this experiment, it was used the sodium salt of the HA-HMW derivative with a weight average MW comprised between 2500 and 3000 KD, prepared as per EP0716688.

20 g HA-HMW was solubilized in 1 L aqueous buffer made from monobasic sodium phosphate (0.05 g), bibasic sodium phosphate (0.6 g), sodium chloride (8.5 g) with a pH of 7.4. 20 g CS (Seikagaku Kogyo, Tokyo) having a MW of 50-60 KD was added thereto, the mixture was subjected to mechanical stirring at 40° C. for 8 hrs until the complete and homogeneous solubilization of the two components.

The mixture was cooled to room temperature and then its moduli were determined by using a Thermo Haake Mars II Rheometer at 20° C.

The values were measured in Pa from 0.01 to 100 rad/sec, at fixed strain values of 10%. All the samples were processed with the Haake Rheowin Job Manager 4.0 software.

Figure 4:
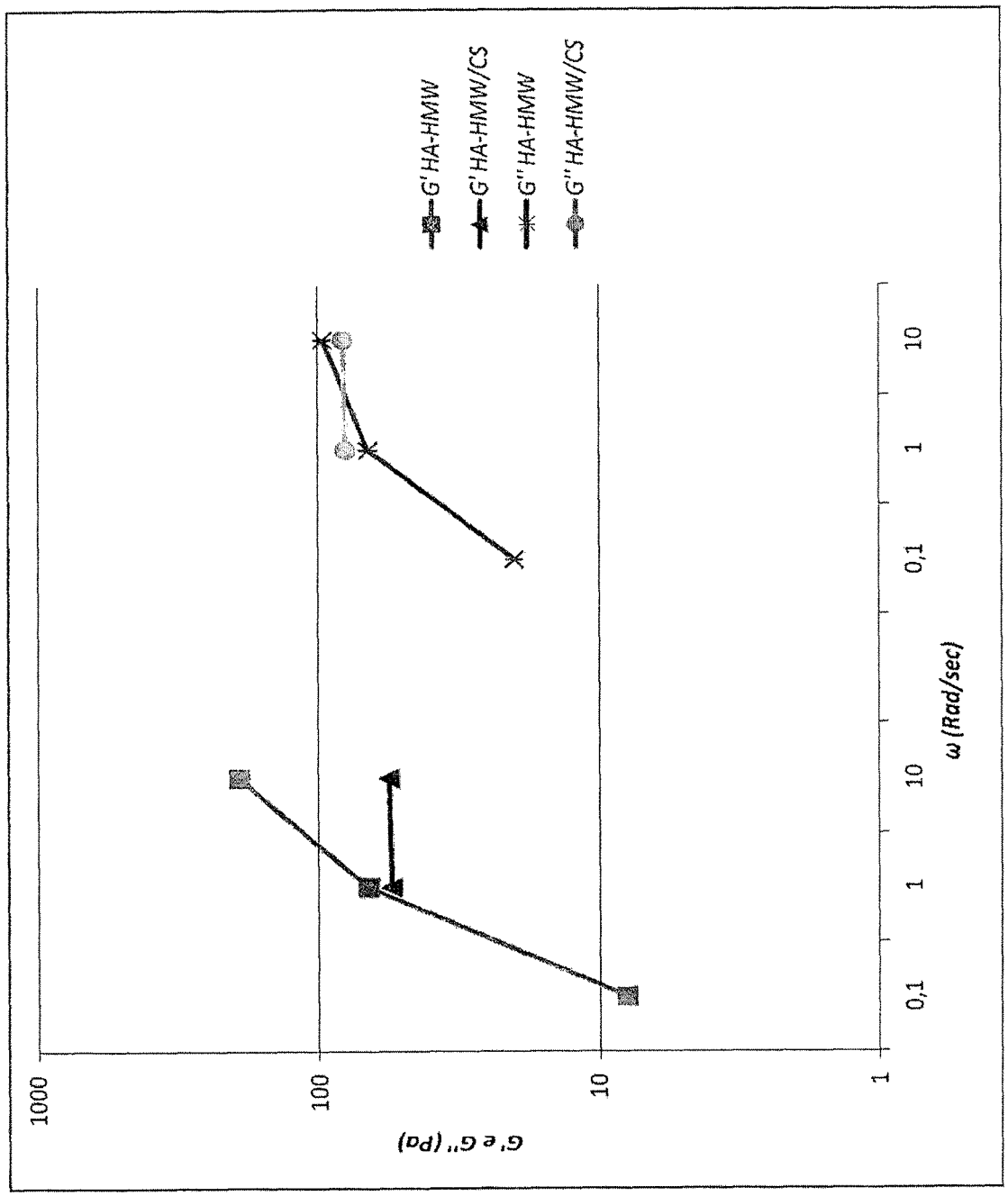
FIG. 4 shows G' and G" values in Pa in function of Co in Rad/sec tested on substances as reported in Example 4.

Results: FIG. 4 shows how also the elastic modulus G' of this novel composition significantly decreases while its viscous modulus G" remains unchanged.

Conclusion: as stated above, the experimental data confirm and demonstrate that the combination of CS to the HA derivatives previously listed and tested, determines an unexpected decrease in the elastic modulus of the novel compositions prepared vs. the corresponding modulus of the starting derivatives essayed, with the concurrent significant increase in the viscous modulus (for certain compositions prepared with specific derivatives, such as HAS1), or the substantial "hold" of the aforementioned modulus G" vs. the viscous moduli of the starting HA derivatives. Therefore, there have been obtained pharmaceutical compositions having rheological features specific to a viscosupplementation agent wherein the viscous component is proportionally increased with respect to the starting derivative, such combination will thus be capable of a greater resistance to frictions and will show a greater ability of joint lubrication, therefore, it may be used as a viscous lubricant by combining the highly anti-inflammatory properties of CS and the anti-inflammatory capabilities of HA derivatives shown previously. For these reasons, the novel compositions can be used in the treatment and/or therapy of the above-listed diseases such as, for example, in the intra-articular therapy of OA and loss of subchondral bone, in the locoregional treatment and/or therapy of diseases such as osteoporosis, particularly of transient regional osteoporosis and finally as a washing liquid and therefore as a substitute of synovial fluid after osteochondral surgery.

The invention claimed is:

1. A method for intraarticular washing comprising rinsing intraarticularly with a viscous liquid consisting of chondroitin sulfate (CS) and hyaluronic acid (HA) amides with amines of the aliphatic, araliphatic, cycloaliphatic, aromatic, cyclic and heterocyclic series, with a percentage of amidation in the range from 0.1 to 10%;

and excipients and/or diluents.

2. A therapeutic method for the treatment of disorders and/or diseases selected from the group consisting of: osteoarthrosis, subchondral damage, osteroporosis and particularly transient regional osteoporosis, osteochondral damage from trauma/microtrauma, synovitis and tenosynovitis, tendinitis and/or tendinosis comprising administering to a subject in need thereof intra-articularly or loco-regionally a therapeutically effective amount of a viscous lubricant consisting of chondroitin sulfate (CS) and hyaluronic acid (HA) amide with hexadecylamine, with a percentage of amidation in the range from 0.1 to 10%; and excipients and/or diluents, wherein the addition of CS with the HA amide is extemporaneous, occurring either just before the intra-articular or locoregional administration or directly within the treatment site, following the separate administration of the two components.

3. The therapeutic method according to claim 1, wherein the combination of CS with the HA amide is extemporaneous, occurring either just before the intra-articular washing or directly during the intraarticular washing, following the separate administration of the two components.

4. A method for intraarticular washing comprising rinsing intraarticularly with a viscous liquid comprising chondroitin sulfate (CS) and hyaluronic acid (HA) amides with amines of the aliphatic, araliphatic, cycloaliphatic, aromatic, cyclic and heterocyclic series, with a percentage of amidation in the range from 0.1 to 10%, wherein the viscous component is proportionally increased with respect to the starting HA amide.

* * * * *